United States Patent
Suzuki

(10) Patent No.: US 7,905,837 B2
(45) Date of Patent: Mar. 15, 2011

(54) ULTRASOUND DIAGNOSTIC APPARATUS

(75) Inventor: Yoichi Suzuki, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 755 days.

(21) Appl. No.: 11/848,771

(22) Filed: Aug. 31, 2007

(65) Prior Publication Data
US 2008/0058645 A1 Mar. 6, 2008

(30) Foreign Application Priority Data
Sep. 4, 2006 (JP) ................................ 2006-238878

(51) Int. Cl.
A61B 8/00 (2006.01)
A61B 8/14 (2006.01)
(52) U.S. Cl. ....................................... 600/441; 600/454
(58) Field of Classification Search .................... 600/441
See application file for complete search history.

(56) References Cited

U.S. PATENT DOCUMENTS
5,682,896 A 11/1997 Scheib et al.
6,390,984 B1 5/2002 Pan et al.
6,599,244 B1 7/2003 Epps et al.

FOREIGN PATENT DOCUMENTS
JP 2005-095278 4/2005

Primary Examiner — Eric F Winakur
Assistant Examiner — Hien Nguyen
(74) Attorney, Agent, or Firm — Armstrong Teasdale LLP

(57) ABSTRACT

An ultrasound diagnostic apparatus includes: an ultrasound probe capable of 2D scanning and 3D scanning; a transceiver device which drives said ultrasound probe to perform 2D scanning and 3D scanning of the inside of a subject with an ultrasound beam; a storage device which stores 3D data obtained by said 3D scanning; a display device which displays on a display device a 3D image resulting from the projection of said stored 3D data, the position of the 2D scanning plane for Doppler measurement, and a Doppler cursor in a prescribed projecting direction; an instruction-responsive altering device which accepts an instruction from the operator and alters said projecting direction and the position of said Doppler cursor in accordance with the instruction; and a Doppler measurement device which performs Doppler measurement by using the finalized position of the 2D scanning plane for Doppler measurement and the Doppler cursor.

19 Claims, 8 Drawing Sheets

ULTRASOUND DIAGNOSTIC APPARATUS

CROSS REFERENCE TO RELATED APPLICATIONS

This application claims the benefit of Japanese Application No. 2006-238878 filed Sep. 4, 2006.

BACKGROUND OF THE INVENTION

The present invention relates to an ultrasound diagnostic apparatus, and more particularly to an ultrasound diagnostic apparatus that makes possible ready checking, when setting the Doppler cursor or the angle cursor, of whether or not the Doppler cursor or the angle cursor is properly set.

Conventionally known ultrasound diagnostic apparatuses include one that displays on a monitor screen four 2D images resulting from the projection of a 3D (three-dimensional) image of a blood vessel in four projecting directions including the frontal, profile, overhead and oblique directions, lets the operator set the Doppler cursor (sample gate) while watching the displayed image, so sets the posture of a plane passing the Doppler cursor that a blood vessel is included in the plane and then set the angle cursor (correction line) on a 2D image of the plane (see, for instance, Patent Document 1).

[Patent Document 1] Japanese Unexamined Patent Publication No. 2005-95278 ([0069] through [0072]).

The conventional ultrasound diagnostic apparatus described above enables the operator to accurately set the Doppler cursor on a blood vessel, which is a three-dimensional structure, by using four 2D images. The setting of the angle cursor by the operator makes possible accurate 3D angle correction of the Doppler-measured flow rates.

However, it is necessary for the operator to compare the four 2D images to see whether the set Doppler cursor is not off the blood vessel, and this operation is not always easy. There is another problem of difficulty to make sure that the angle cursor is along the direction of the blood vessel.

SUMMARY OF THE INVENTION

It is desirable that the problems described previously are solved.

The invention in its first aspect provides an ultrasound diagnostic apparatus comprising: an ultrasound probe capable of 2D scanning by electronic scanning and 3D scanning by electric scanning or electronic scanning; a transceiver device which drives the ultrasound probe to perform 2D scanning and 3D scanning of the inside of a subject with an ultrasound beam; a storage device which stores 3D data obtained by the 3D scanning; a display device which displays on a display device a 3D image resulting from the projection of the stored 3D data, the position of the 2D scanning plane for Doppler measurement, and a Doppler cursor in a prescribed projecting direction; an instruction-responsive altering device which accepts an instruction from the operator and alters the projecting direction and the position of the Doppler cursor in accordance with the instruction; and a Doppler measurement device which performs Doppler measurement by using the finalized position of the 2D scanning plane for Doppler measurement and the Doppler cursor.

In the ultrasound diagnostic apparatus according to the first aspect, the position of the 2D scanning plane for Doppler measurement and the Doppler cursor are displayed over a 3D image. And the operator can see a 3D image in an altered direction of vision by giving an instruction to alter the projecting direction. Therefore, the operator can readily check whether or not the Doppler cursor is properly set. To add, the operator can move the Doppler cursor to an appropriate position by giving an instruction to alter the position of the Doppler cursor.

The invention in its second aspect provides an ultrasound diagnostic apparatus according to the first aspect, wherein the initial position of the Doppler cursor is a preset position.

In the ultrasound diagnostic apparatus according to the second aspect, the Doppler cursor is initially set in the default position irrespective of the current 2D data or 3D data. Since it is sufficient to store the default position, processing is simplified.

The invention in its third aspect provides an ultrasound diagnostic apparatus according to the first aspect, wherein the initial position of the Doppler cursor is the position of a blood vessel extracted from data.

In the ultrasound diagnostic apparatus according to the third aspect, a blood vessel passing the 2D scanning plane for Doppler measurement is extracted on the basis of current data, and the Doppler cursor is set in that position. The operator's labor can be saved to some extent.

The invention in its fourth aspect provides an ultrasound diagnostic apparatus according to any of the first through third aspects, wherein the position of the 2D scanning plane for the Doppler measurement is the position of the scanning plane where 2D scanning is being performed on a real time basis.

In the ultrasound diagnostic apparatus according to the fourth aspect, the operator can move the 2D scanning plane for Doppler measurement by moving the ultrasound probe.

The invention in its fifth aspect provides an ultrasound diagnostic apparatus according to the fourth aspect further provided with a position correcting device which corrects the position of the 2D scanning plane according to correlation between the 3D data and real time 2D data obtained by performing 2D scanning on the real time basis.

In the ultrasound diagnostic apparatus according to the fifth aspect, even if the subject moves or the operator has unintentionally moved the ultrasound probe, the 2D scanning plane for Doppler measurement can be caused to follow such a motion.

The invention in its sixth aspect provides an ultrasound diagnostic apparatus according to any of the first through third aspects, wherein the position of the 2D scanning plane for the Doppler measurement is the position of the 2D scanning plane designated by the operator.

In the ultrasound diagnostic apparatus according to the sixth aspect, since it is sufficient to store the position of the 2D scanning plane designated by the operator, processing is simplified.

The invention in its seventh aspect provides an ultrasound diagnostic apparatus according to the sixth aspect, wherein the 3D data are real time 3D data obtained by performing 3D scanning on a real time basis.

In the ultrasound diagnostic apparatus according to the seventh aspect, since the operator can see the real time 3D image (or 4D image), even if the subject moves or the operator has unintentionally moved the ultrasound probe, it can be accurately checked whether or not the position of the Doppler cursor is appropriate.

The invention in its eighth aspect provides an ultrasound diagnostic apparatus according to the seventh aspect, further provided with a position correcting device which corrects the position of the 2D scanning plane according to correlation between 2D data obtained on the 2D scanning plane and the real time 3D data.

In the ultrasound diagnostic apparatus according to the eighth aspect, even if the subject moves or the operator has unintentionally moved the ultrasound probe, the 2D scanning plane for Doppler measurement can be caused to follow such a motion.

The invention in its ninth aspect provides an ultrasound diagnostic apparatus comprising: an ultrasound probe capable of 2D scanning by electronic scanning and 3D scanning by electric scanning or electronic scanning; a transceiver device which drives the ultrasound probe to perform 2D scanning and 3D scanning of the inside of a subject with an ultrasound beam; a storage device which stores 3D data obtained by the 3D scanning; a display device which displays on a display device a 3D image resulting from the projection of the stored 3D data and an angle cursor representing the direction of the blood vessel at a Doppler observation point; an instruction-responsive altering device which accepts an instruction from the operator and alters the projecting direction and the direction of the angle cursor in accordance with the instruction; a Doppler measurement device which performs Doppler measurement at the Doppler observation point; and a correcting device which corrects the result of the Doppler measurement according to the angle formed by the direction of the ultrasound beam according to the Doppler measurement and the finalized direction of the angle cursor.

In the ultrasound diagnostic apparatus according to the ninth aspect, the angle cursor is displayed over a 3D image. And the operator can see a 3D image in an altered direction of vision by giving an instruction to alter the projecting direction. Therefore, the operator can readily check whether or not the angle cursor is properly set. To add, the operator can move the angle cursor to an appropriate position by giving an instruction to alter the position of the angle cursor.

The invention in its tenth aspect provides an ultrasound diagnostic apparatus according to the ninth aspect, wherein the initial position of the angle cursor is a preset position.

In the ultrasound diagnostic apparatus according to the tenth aspect, the Doppler cursor is initially set in the default direction irrespective of the current 2D data or 3D data. Since it is sufficient to store the default direction, processing is simplified.

The invention in its eleventh aspect provides an ultrasound diagnostic apparatus according to the ninth aspect, wherein the initial direction of the angle cursor is the direction of a blood vessel extracted by analyzing 3D data.

In the ultrasound diagnostic apparatus according to the eleventh aspect, the direction of the blood vessel to be Doppler-measured is extracted on the basis of current 3D data, and the angle cursor is set in that direction. The operator's labor can be saved to some extent.

The invention in its twelfth aspect provides an ultrasound diagnostic apparatus according to any of the ninth through eleventh aspects, wherein the display device also displays the position of the 2D scanning plane for Doppler measurement and the Doppler cursor.

In the ultrasound diagnostic apparatus according to the twelfth aspect, both the position of the 2D scanning plane for Doppler measurement and the position of the Doppler cursor can be checked at the same time.

The invention in its thirteenth aspect provides an ultrasound diagnostic apparatus according to the twelfth aspect, wherein the position of the 2D scanning plane for the Doppler measurement is the position of the scanning plane where 2D scanning is being performed on a real time basis.

In the ultrasound diagnostic apparatus according to the thirteenth aspect, the operator can move the 2D scanning plane for Doppler measurement by moving the ultrasound probe.

The invention in its fourteenth aspect provides an ultrasound diagnostic apparatus according to the thirteenth aspect, further provided with position correcting device which corrects the position of the 2D scanning plane according to correlation between the 3D data and real time 2D data obtained by performing 2D scanning on the real time basis.

In the ultrasound diagnostic apparatus according to the fourteenth aspect, even if the subject moves or the operator has unintentionally moved the ultrasound probe, the 2D scanning plane for Doppler measurement can be caused to follow such a motion.

The invention in its fifteenth aspect provides an ultrasound diagnostic apparatus according to any of the ninth through eleventh aspects, wherein the position of the 2D scanning plane for the Doppler measurement is the position of the 2D scanning plane designated by the operator.

In the ultrasound diagnostic apparatus according to the fifteenth aspect, since it is sufficient to store the position of the 2D scanning plane designated by the operator, processing is simplified.

The invention in its sixteenth aspect provides an ultrasound diagnostic apparatus according to the sixteenth aspect, wherein the 3D data are real time 3D data obtained by performing 3D scanning on a real time basis.

In the ultrasound diagnostic apparatus according to the sixteenth aspect, since the operator can see a 3D image on a real time basis, even if the subject moves or the operator has unintentionally moved the ultrasound probe, the operator can readily check visually whether or not the angle cursor is properly set.

The invention in its seventeenth aspect provides an ultrasound diagnostic apparatus according to the sixteenth aspect, further provided with position correcting device which corrects the position of the 2D scanning plane according to correlation between 2D data obtained on the 2D scanning plane and the real time 3D data.

In the ultrasound diagnostic apparatus according to the seventeenth aspect, even if the subject moves or the operator has unintentionally moved the ultrasound probe, the 2D scanning plane for Doppler measurement can be caused to follow such a motion.

The ultrasound diagnostic apparatus according to the invention enables the operator to see the Doppler cursor and the angle cursor on a 3D image in an altered direction of the line of sight by giving an instruction to alter the projecting direction. Therefore, it can be readily checked whether or not the Doppler cursor and the angle cursor are appropriately set.

The ultrasound diagnostic apparatus according to the invention can be utilized for Doppler measurement of the flow rate of blood stream.

Further objects and advantages of the present invention will be apparent from the following description of the preferred embodiments of the invention as illustrated in the accompanying drawings.

DETAILED DESCRIPTION OF THE INVENTION

The invention will be described in further detail below with reference to the illustrated modes for implementation thereof. Incidentally, this is nothing to limit the invention.

Embodiment 1

Figure 1:
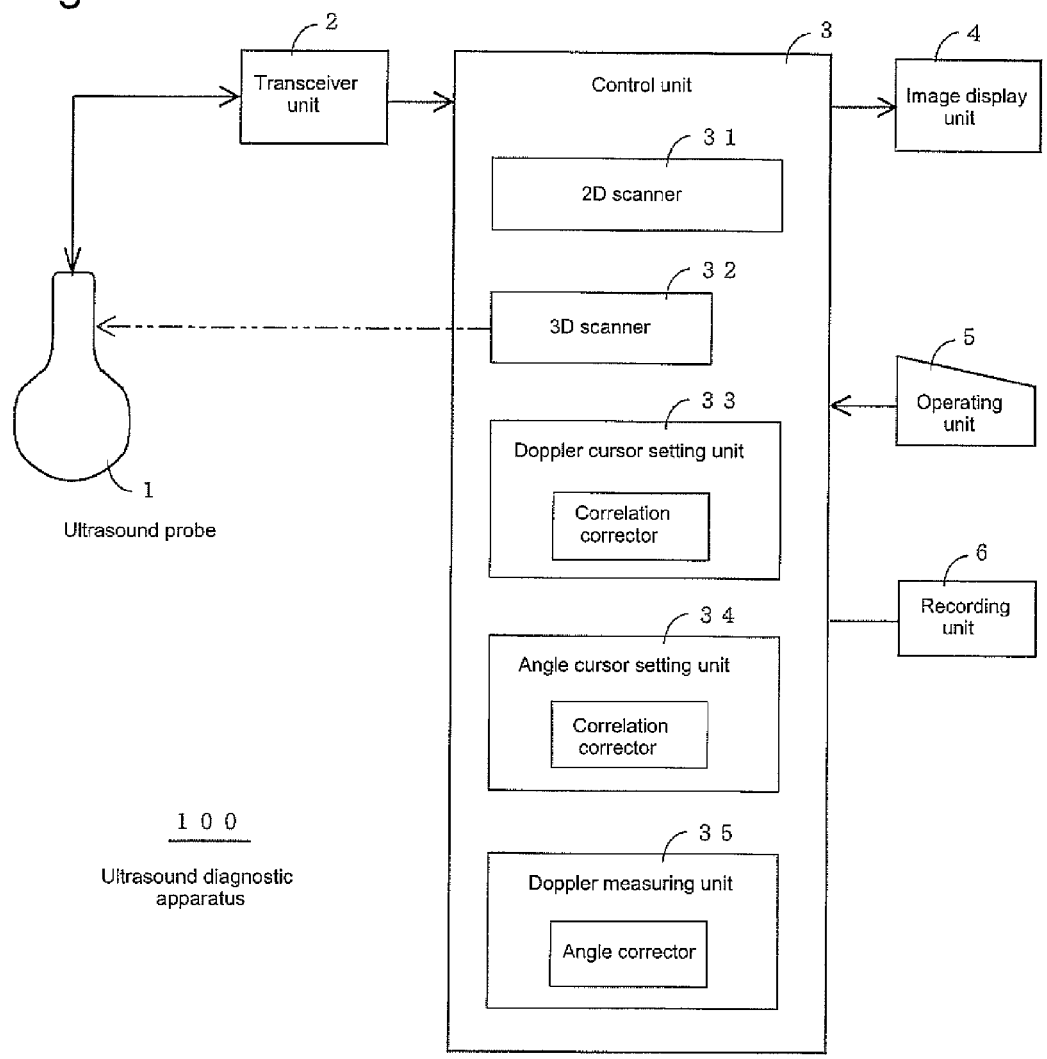
FIG. 1 is a diagram illustrating the configuration of an ultrasound diagnostic apparatus pertaining to Embodiment 1.

FIG. 1 illustrates the configuration of an ultrasound diagnostic apparatus 100 pertaining to Embodiment 1.

This ultrasound diagnostic apparatus 100 is provided with an ultrasound probe 1 capable of 2D scanning by electronic scanning and 3D scanning by electric scanning (motor-driven scanning) or electronic scanning, a transceiver unit 2 which drives the ultrasound probe 1 to perform 2D scanning and 3D scanning of the inside of a subject with an ultrasound beam, a control unit 3, an image display unit 4 for displaying 2D images and the like, an operating unit 5 to enable the operator to give instructions and data, and a recording unit 6 for recording 2D images and the like.

A 2D scanner 31 of the control unit 3 controls 2D scanning, stores 2D data and generates 2D images.

A 3D scanner 32 controls 3D scanning, stores 3D data and generates 3D images resulting from the projection of 3D data in a prescribed projecting direction.

A Doppler cursor setting unit 33 executes processing to set the Doppler cursor to be described later. It includes a correlation corrector that determines correlation between 2D data and 3D data and corrects the positional relationship.

An angle cursor setting unit 34 executes processing to set the angle cursor to be described later. It includes a correlation corrector which determines correlation between 2D data and 3D data and corrects the positional relationship.

A Doppler measuring unit 35 Doppler-measures flow rates with the position of the Doppler cursor as the Doppler measuring point, and generates a flow rate distribution image (a graph of variations of the flow rate distribution over time). The unit includes an angle corrector that corrects the results of Doppler measurement according to the angle formed by the ultrasonic beam and the angle cursor.

Figure 2:
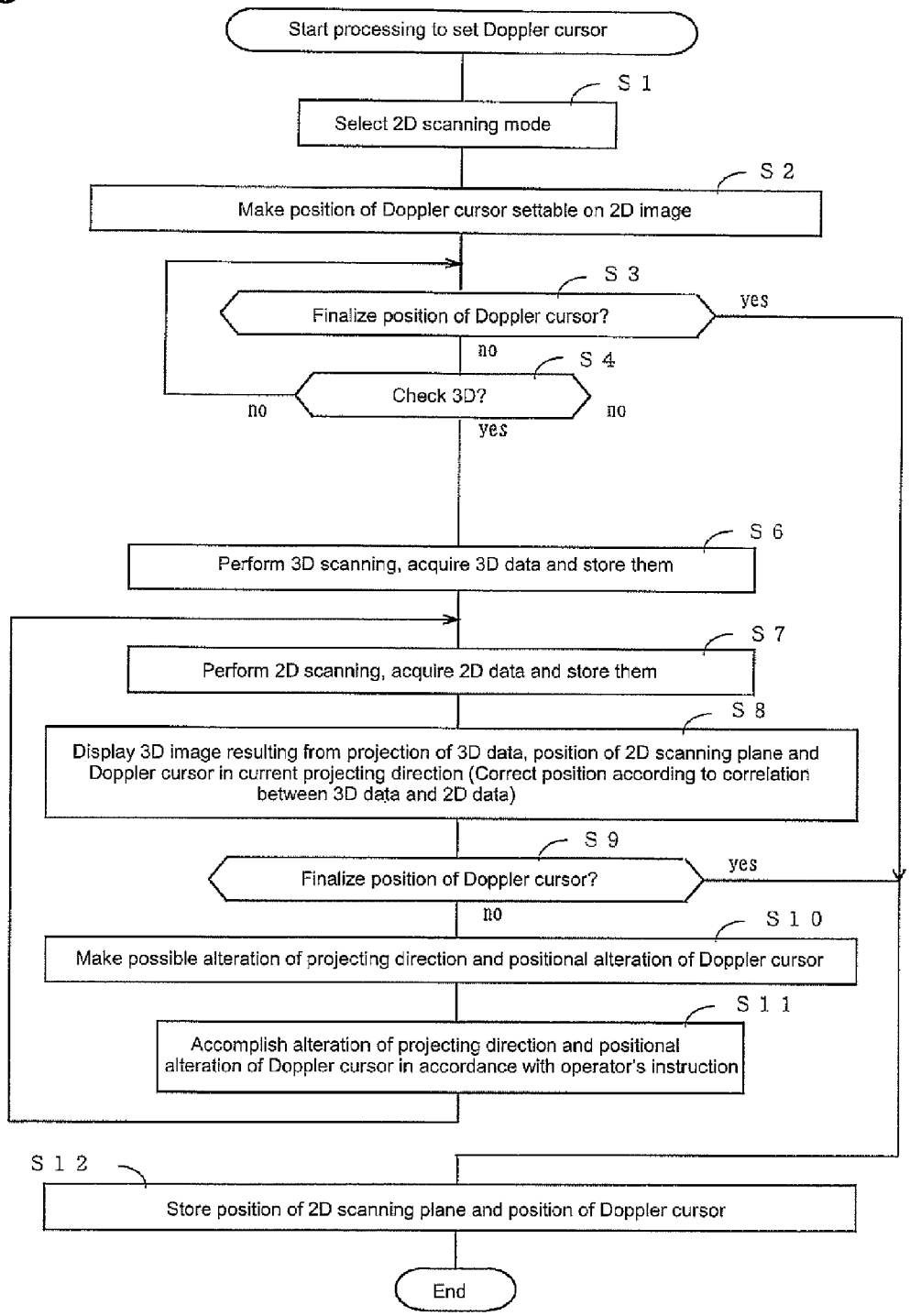
FIG. 2 is a flow chart showing the processing to set the Doppler cursor pertaining to Embodiment 1.

FIG. 2 is a flow chart showing the processing to set the Doppler cursor by the Doppler cursor setting unit 33.

At step S1, a 2D scanning mode is selected. Namely, the 2D scanner 31 acquires 2D data by 2D scanning, stores them and generates a 2D image. Then, the 2D image is displayed on the image display unit 4. The position of the 2D scanning plane in the 2D scanning mode is supposed to be the default position of the scanning plane which is preset.

Figure 3:
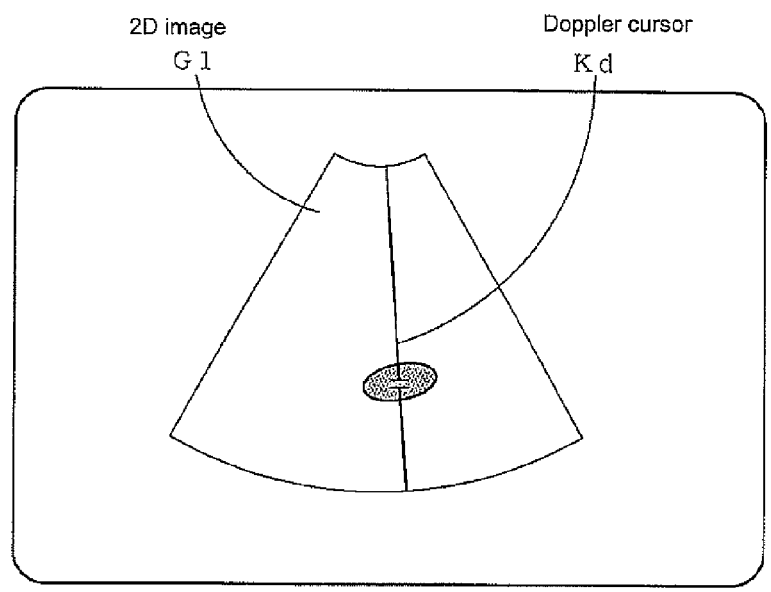
FIG. 3 is an exemplary drawing showing a screen display of a 2D image and the Doppler cursor.

At step S2, as shown in FIG. 3, a Doppler cursor Kd is displayed over the 2D image G1. The position in which the Doppler cursor Kd is displayed first is either a preset default position or the position of the largest blood vessel obtained by analyzing and extracting from 2D data (or the 2D image instead). And an operation by the operator to alter the position of the Doppler cursor Kd is accepted. Incidentally, the position of the Doppler cursor Kd is to be defined as a position on the 2D scanning plane.

At step S3, if the operator performs an operation to finalize the position of the Doppler cursor, the processing advances to step S12 or, if the operation is not done, it advances to step S4.

At step S4, if the operator performs an operation to check the position of Doppler cursor with a 3D image, the processing advances to step S6 or, if the operation is not done, it returns to step S3.

At step S6, the 3D scanner 32 acquires 3D data by 3D scanning and stores them.

Figure 4:
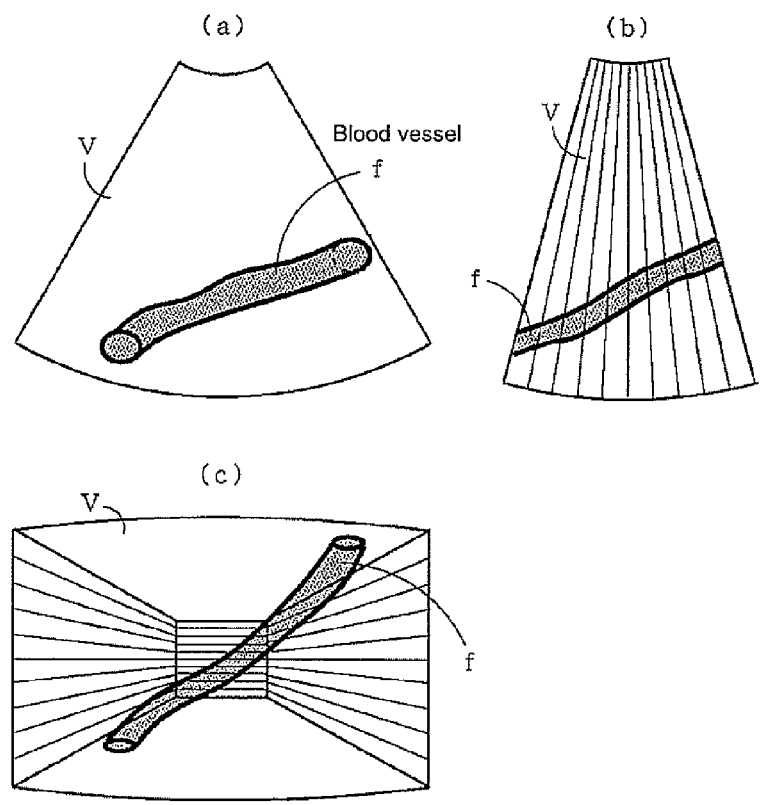
FIGS. 4(a), 4(b), and 4(c) are conceptual drawings of 3D data.

FIG. 4 conceptually show 3D data V. FIG. 4(a) shows a front view, 4(b), a profile and 4(c), a top view. Reference sign f denotes a blood vessel.

At step S7, the 2D scanner 31 acquires 2D data by 2D scanning and stores them. The position of the 2D scanning plane then is to be that of the preset default scanning plane.

At step S8, a 3D image resulting from the projection of 3D data, the position of the 2D scanning plane and the Doppler cursor in the current projecting direction is displayed. Incidentally, the position of the 2D scanning plane is corrected according to correlation between the 3D data and the 2D data. Further, the initial projecting direction is to be the preset default direction.

Figure 5:
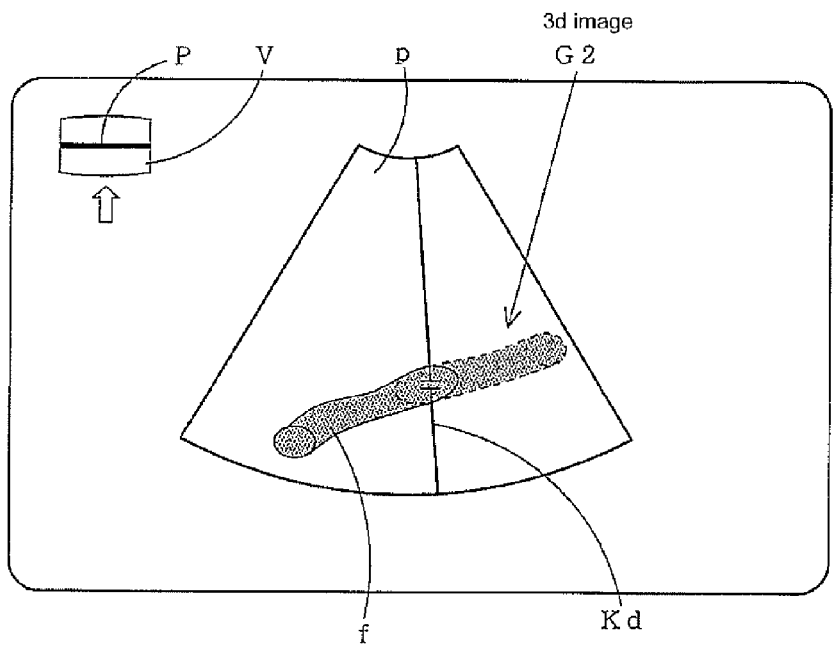
FIG. 5 is an exemplary drawing showing a screen display of a 3D image and the Doppler cursor.

FIG. 5 shows an example of 3D image G2. Reference sign p denotes the position of the 2D scanning plane. In the top left of the screen, a plan of three-dimensional data V, the position P of the 2D scanning plane and an arrow indicating the projecting direction are displayed.

At step S9, if the operator performs an operation to finalize the position P of the Doppler cursor, the processing advances to step S12 or, if the operation is not done, it advances to step S10.

At step S10, alteration of the projecting direction and positional alteration of the Doppler cursor by the operator are accepted.

At step S11, alteration of the projecting direction and positional alteration of the Doppler cursor are accomplished in accordance with the instruction of the operator. Then, the processing returns to step S7.

Figure 6:
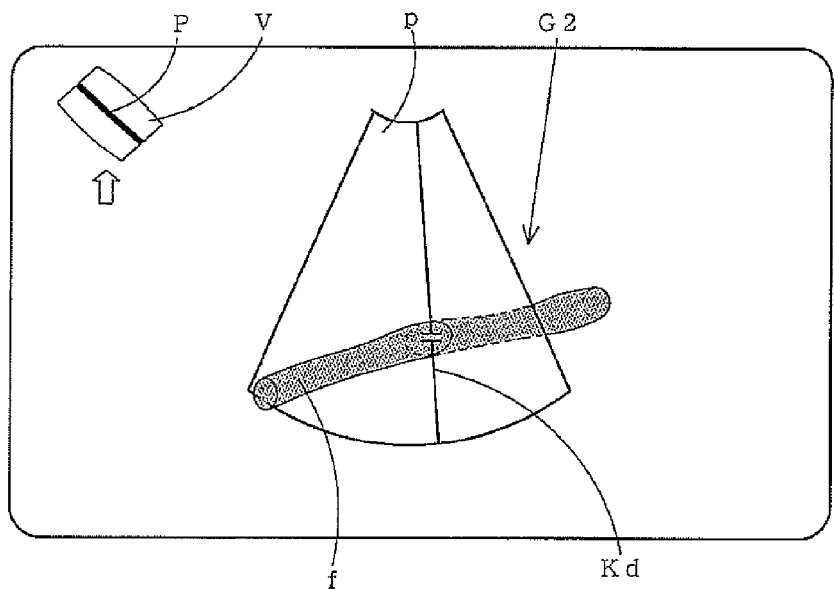
FIG. 6 is an exemplary drawing showing a screen display of a 3D image altered in projecting direction and the Doppler cursor.

FIG. 6 shows a 3D image G2 after the projecting direction has been altered. Incidentally, though the projecting direction is turned in the horizontal direction in this example, it may as well be turned in the vertical direction.

At step S12, the current position of the 2D scanning plane and the position of the Doppler cursor are stored. Then, the processing is ended.

Figure 7:
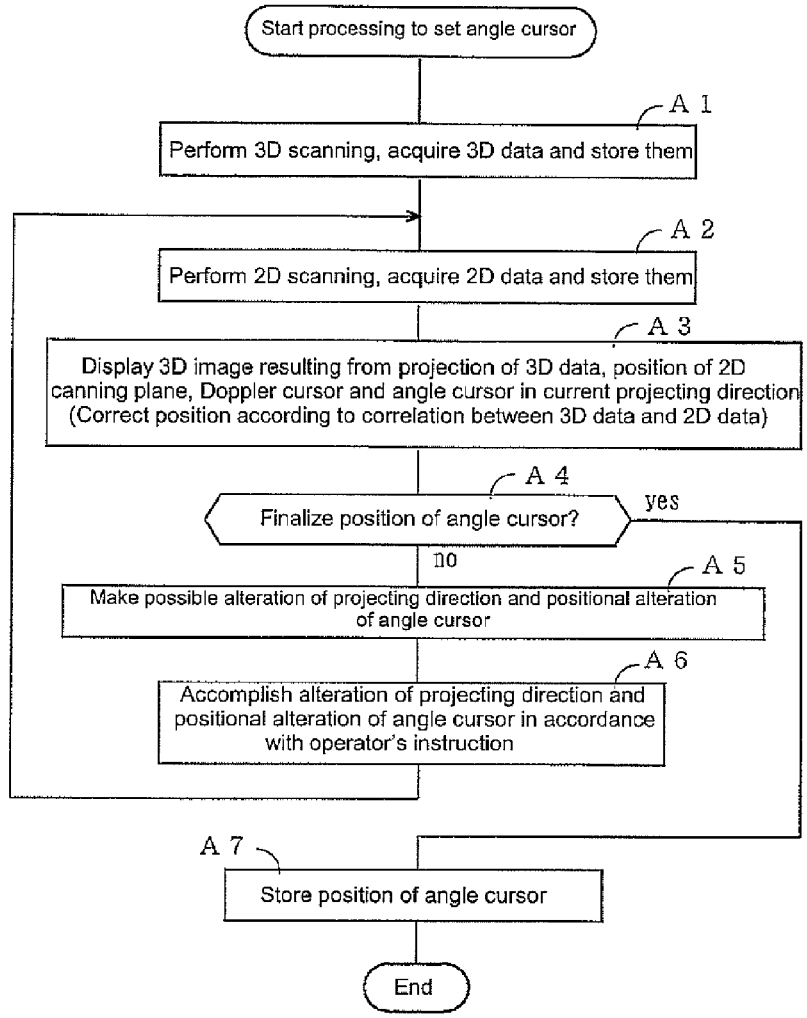
FIG. 7 is a flow chart of the processing to set the angle cursor pertaining to Embodiment 1.

FIG. 7 is a flow chart of the processing to set the angle cursor by the angle cursor setting unit 34.

At step A1, the 3D scanner 32 acquires 3D data by 3D scanning and stores them.

At step A2, the 2D scanner 31 acquires 2D data by 2D scanning and stores them. The position of the 2D scanning plane then is supposed to be the position stored at the time of setting the Doppler cursor.

At step A3, a 3D image resulting from the projection of 3D data, the position of the 2D scanning plane, the Doppler cursor and the angle cursor in the current projecting direction is displayed. Incidentally, the position of the 2D scanning plane is corrected according to correlation between the 3D data and the 2D data. Further, the initial projecting direction is to be the preset default direction. The position of the Doppler cursor is to be the position stored at the time of setting the Doppler cursor. Further, the center of the angle cursor is supposed to pass the Doppler measurement point, and the initial position is to be either the preset default direction or the direction of the blood vessel passing the Doppler measurement point extracted by analyzing the 3D data.

Figure 8:
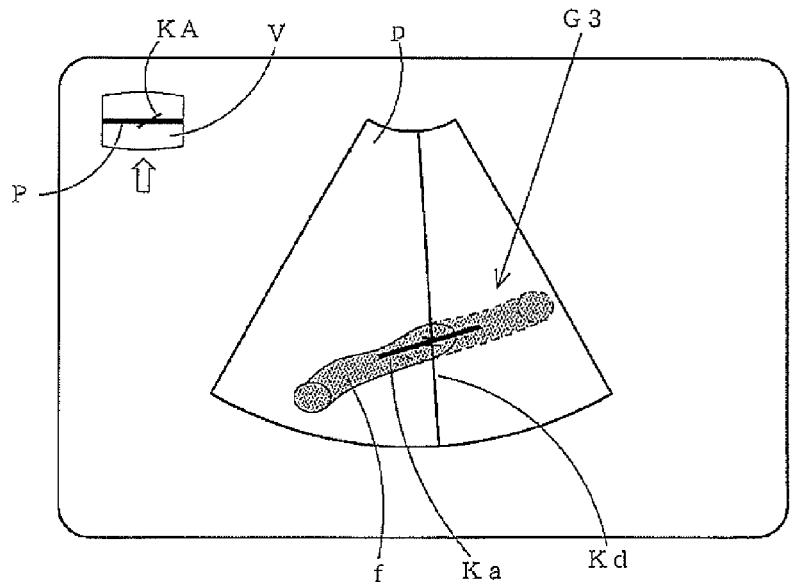
FIG. 8 is an exemplary drawing showing a screen display of a 3D image and the angle cursor.

FIG. 8 shows an example of 3D image G3. Reference sign Ka denotes an angle cursor. In the top left of the screen, a plan of three-dimensional data V, the position P of the 2D scanning plane, an arrow indicating the projecting direction and a plan KA of the angle cursor Ka are displayed.

At step A4, if the operator performs an operation to finalize the position of the angle cursor, the processing advances to step A7 or, if the operation is not done, it advances to step A5.

At step A5, alteration of the projecting direction and positional alteration of the angle cursor by the operator are accepted.

At step A6, alteration of the projecting direction and positional alteration of the angle cursor are accomplished in accordance with the instruction of the operator. Then, the processing returns to step A2.

Figure 9:
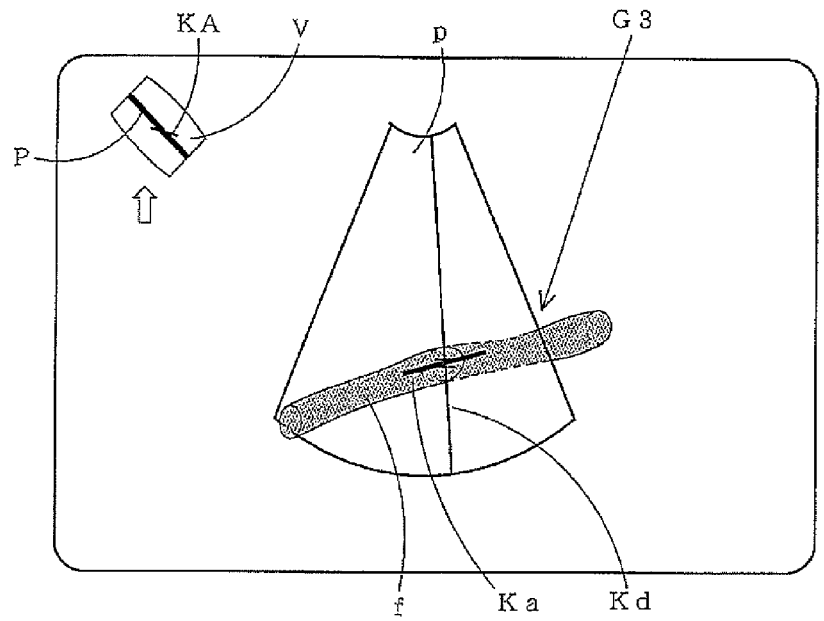
FIG. 9 is an exemplary drawing showing a screen display of a 3D image altered in projecting direction and the angle cursor.

FIG. 9 shows a 3D image G4 after the projecting direction has been altered. Incidentally, though the projecting direction is turned in the horizontal direction in this example, it may as well be turned in the vertical direction.

At step A7, the current direction of the angle cursor is stored. Then, the processing is ended.

Figure 10:
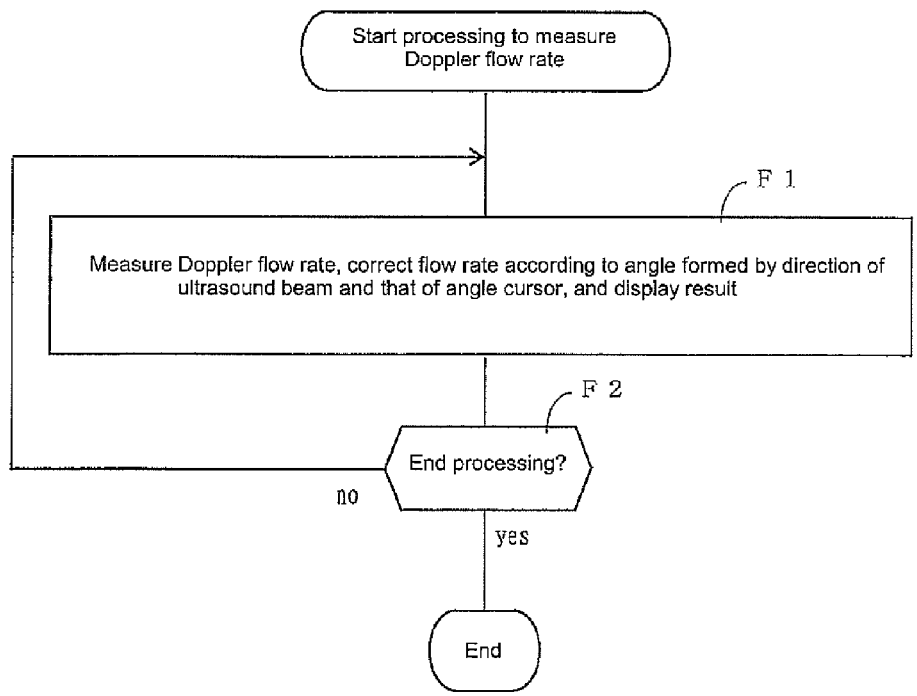
FIG. 10 is a flow chart showing the processing to measure the Doppler flow rate pertaining to Embodiment 1.

FIG. 10 is a flow chart showing the processing to set the Doppler flow rate by the Doppler measuring unit 35.

At step F1, the flow rate of the blood stream is obtained by performing Doppler measurement at the Doppler measurement point defined by the Doppler cursor. Since the result of this measurement is the ultrasound beam-direction component of the actual flow rate, the actual flow rate is obtained by correcting the flow rate according to the angle formed by the direction of the ultrasound beam and that of the angle cursor. Then, a flow rate distribution image is generated and displayed on the image display unit 4.

At step F2, if the operator performs an operation to end the processing, the processing is ended or, if not, the processing returns to step F1.

The ultrasound diagnostic apparatus 100 of Embodiment 1 enables an instruction by the operator for alteration of the projecting direction to make visible the Doppler cursor and the angle cursor on a 3D image altered in the direction of the line of sight. Therefore, it can be readily checked whether or not the Doppler cursor and the angle cursor are appropriately set.

Embodiment 2

Although the position of the 2D scanning plane is updated on a real time basis in the processing to set the Doppler cursor for Embodiment 1, the 3D data are not updated on a real time basis.

In the processing to set the Doppler cursor for Embodiment 2, the 3D data are updated on a real time basis, but the position of the 2D scanning plane is not updated on a real time basis.

Figure 11:
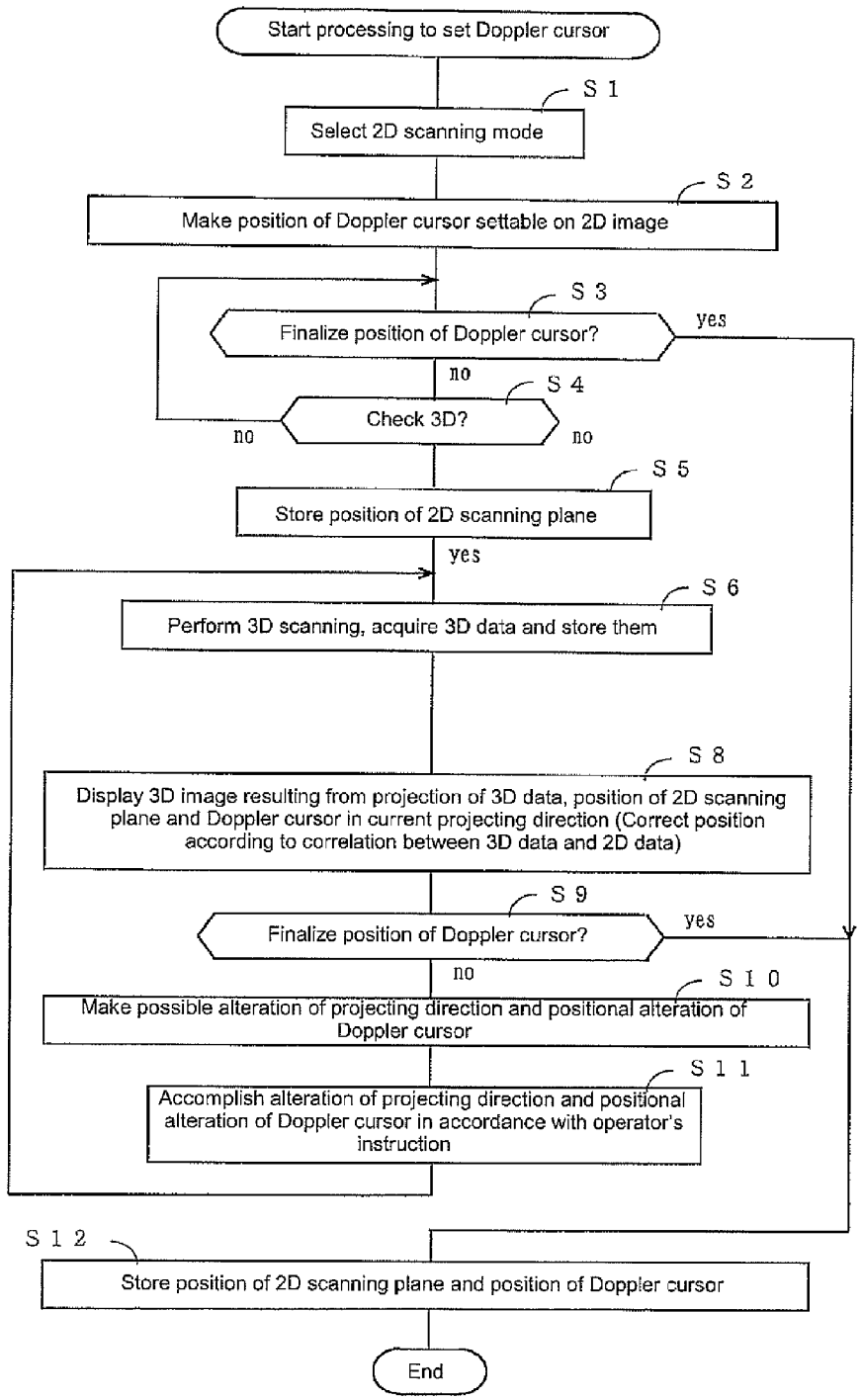
FIG. 11 is a flow chart showing the processing to set the Doppler cursor pertaining to Embodiment 2.

FIG. 11 is a flow chart showing the processing to set the Doppler cursor pertaining to Embodiment 2.

Steps S1, S2, and S3 are the same as in Embodiment 1.

At step S4, if the operator performs an operation to check the position of the Doppler cursor by a 3D image, the processing advances to step S5 or, if the operation is not done, it returns to step S3.

At step S5, the current position of the 2D scanning plane is stored. Then, the processing advances to step S6.

At step S6, the 3D scanner 32 acquires 3D data by 3D scanning and stores them. Then, the processing advances to step S8.

Steps S8, S9, and S10 are the same as in Embodiment 1.

At step S11, alteration of the projecting direction and positional alteration of the Doppler cursor are accomplished in accordance with the instruction of the operator. Then, the processing returns to step S6.

At step S12 a position of the 2D scanning plane and a position of the Doppler cursor are stored.

Embodiment 3

In the processing to set the angle cursor for Embodiment 1, the position of the 2D scanning plane is updated on a real time basis, but the 3D data are not updated on a real time basis.

In the processing to set the angle cursor for Embodiment 3, the 3D data updated on a real time basis, but the position of the 2D scanning plane is not updated on a real time basis.

Figure 12:
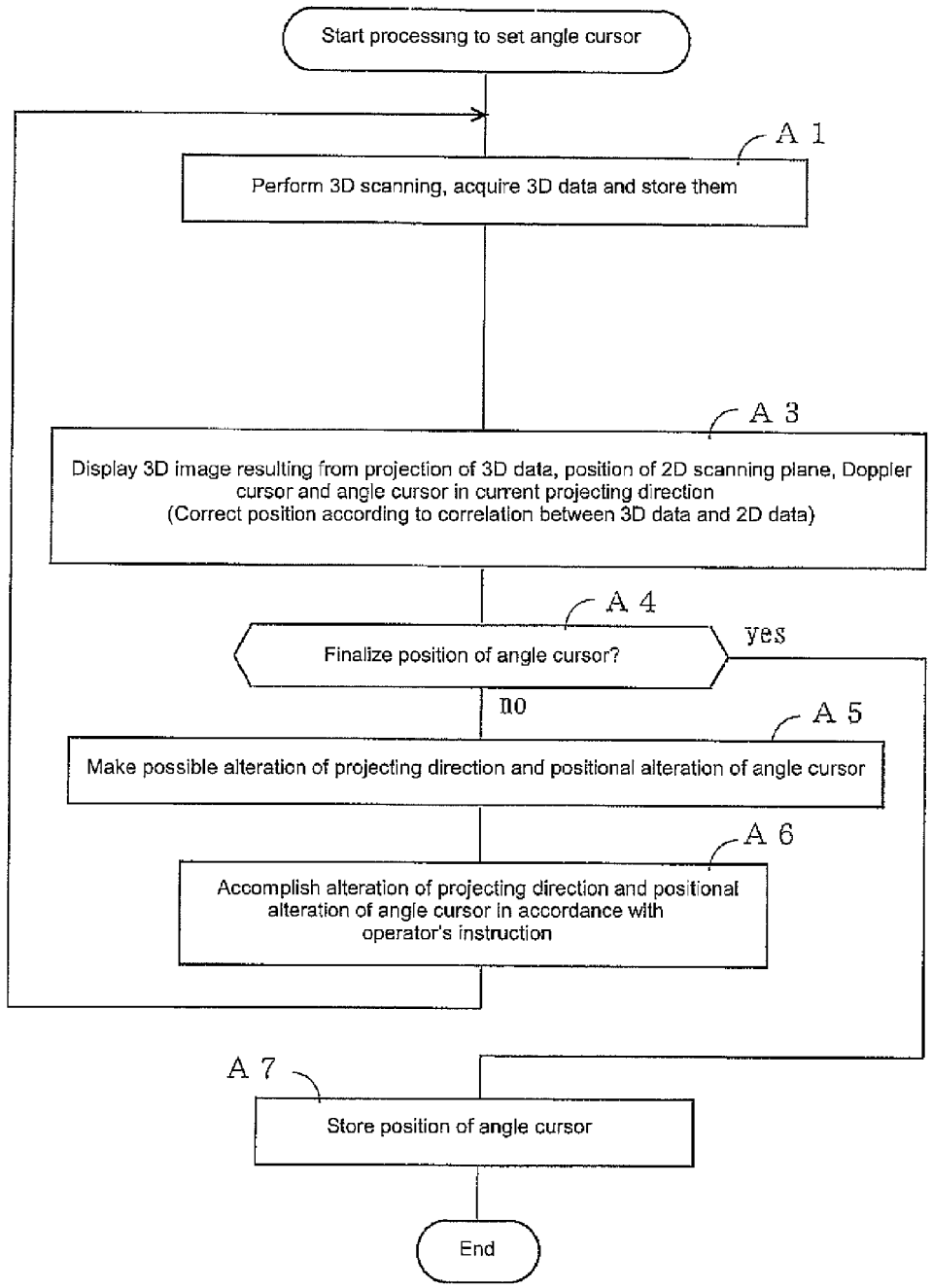
FIG. 12 is a flow chart showing the processing to set the angle cursor pertaining to Embodiment 3.

FIG. 12 is a flow chart showing the processing to set the angle cursor pertaining to Embodiment 3.

At step A1, the 3D scanner 32 acquires 3D data by 3D scanning and stores them. Then, the processing advances to step A3.

Steps A3, A4, and A5 are the same as in Embodiment 1.

At step A6, alteration of the projecting direction and positional alteration of the angle cursor are accomplished in accordance with the instruction of the operator. Then, the processing returns to step A1.

Step A7 is the same as in Embodiment 1.

Embodiment 4

The processing may return from step S11 to step S6 of Embodiment 1. In this case, the position of the 2D scanning plane and the 3D data are updated on a real time basis.

Embodiment 5

The processing may return from step A6 to step A1 of Embodiment 1. In this case, the position of the 2D scanning plane and the 3D data are updated on a real time basis.

Many widely different embodiments of the invention may be configured without departing from the spirit and the scope of the present invention. It should be understood that the present invention is not limited to the specific embodiments described in the specification, except as defined in the appended claims.

The invention claimed is:

1. An ultrasound diagnostic apparatus comprising:
an ultrasound probe configured to perform two-dimensional (2D) scanning and three-dimensional (3D) scanning;
a transceiver device configured to drive said ultrasound probe to perform 2D scanning and 3D scanning of a subject with an ultrasound beam;
a storage device configured to store 3D data obtained by 3D scanning;
a display device configured to display a combined image including a 3D image resulting from projection of the stored 3D data, an initial position of a 2D scanning plane for use in Doppler measurement, and a Doppler cursor in a prescribed projecting direction;

an instruction-responsive altering device configured to accept an instruction from an operator and to alter the projecting direction and a position of the Doppler cursor in accordance with the instruction; and a Doppler measurement device configured to perform Doppler measurement using a finalized position of the 2D scanning plane and the Doppler cursor.

2. The ultrasound diagnostic apparatus according to claim 1, wherein an initial position of the Doppler cursor is a preset position.

3. The ultrasound diagnostic apparatus according to claim 2, wherein the finalized position of the 2D scanning plane is a position of the 2D scanning plane where 2D scanning is being performed in real time.

4. The ultrasound diagnostic apparatus according to claim 3, further comprising a position correcting device configured to correct the initial position of the 2D scanning plane according to a correlation between the 3D data and real time 2D data obtained by performing 2D scanning in real time.

5. The ultrasound diagnostic apparatus according to claim 1, wherein an initial position of the Doppler cursor is a position of a blood vessel extracted from data.

6. The ultrasound diagnostic apparatus according to claim 5, wherein the finalized position of the 2D scanning plane is a position of the 2D scanning plane where 2D scanning is being performed in real time.

7. The ultrasound diagnostic apparatus according to claim 1, wherein the finalized position of the 2D scanning plane is a position of the 2D scanning plane where 2D scanning is being performed in real time.

8. The ultrasound diagnostic apparatus according to claim 7, further comprising a position correcting device configured to correct the initial position of the 2D scanning plane according to a correlation between the 3D data and real time 2D data obtained by performing 2D scanning in real time.

9. The ultrasound diagnostic apparatus according to claim 1, wherein the finalized position of the 2D scanning plane is a position of the 2D scanning plane as designated by the operator.

10. The ultrasound diagnostic apparatus according to claim 9, wherein the 3D data is real time 3D data obtained by performing 3D scanning in real time.

11. The ultrasound diagnostic apparatus according to claim 10, further comprising a position correcting device configured to correct the initial position of the 2D scanning plane according to a correlation between 2D data obtained along the 2D scanning plane and the real time 3D data.

12. An ultrasound diagnostic apparatus comprising:

an ultrasound probe configured to perform two-dimensional (2D) scanning and three-dimensional (3D) scanning;

a transceiver device configured to drive said ultrasound probe to perform 2D scanning and 3D scanning of a subject with an ultrasound beam;

a storage device configured to store 3D data obtained by 3D scanning;

a display device configured to display a combined image including a 3D image resulting from projection of stored 3D data and an angle cursor representing a direction of a blood vessel at a Doppler observation point, a position of a 2D scanning plane for use in Doppler measurement, and a Doppler cursor;

an instruction-responsive altering device configured to accept an instruction from an operator and to alter a projecting direction and an initial direction of the angle cursor in accordance with the instruction;

a Doppler measurement device configured to perform Doppler measurement at the Doppler observation point; and a correcting device configured to correct a result of the Doppler measurement according to an angle formed by a direction of the ultrasound beam according to the Doppler measurement and a finalized direction of the angle cursor.

13. The ultrasound diagnostic apparatus according to claim 12, wherein the initial position of the angle cursor is a preset position.

14. The ultrasound diagnostic apparatus according to claim 12, wherein the initial direction of the angle cursor is a direction of the blood vessel extracted from the 3D data.

15. The ultrasound diagnostic apparatus according to claim 12, wherein the position of the 2D scanning plane for said Doppler measurement is the position of the scanning plane where 2D scanning is being performed on a real time basis.

16. The ultrasound diagnostic apparatus according to claim 15, further comprising a position correcting device configured to correct the position of the 2D scanning plane according to a correlation between the 3D data and real time 2D data obtained by performing 2D scanning in real time.

17. The ultrasound diagnostic apparatus according to claim 12, wherein the position of the 2D scanning plane is a position designated by the operator.

18. The ultrasound diagnostic apparatus according to claim 17, wherein the 3D data is real time 3D data obtained by performing 3D scanning in real time.

19. The ultrasound diagnostic apparatus according to claim 18, further comprising a position correcting device configured to correct the position of the 2D scanning plane according to a correlation between 2D data obtained on the 2D scanning plane and the real time 3D data.

* * * * *